United States Patent
Schaffer et al.

(10) Patent No.: US 9,002,659 B2
(45) Date of Patent: Apr. 7, 2015

(54) PRECIOUS METAL TESTING APPARATUS WITH CALIBRATION SYSTEM

(76) Inventors: Jarrett Schaffer, Allentown, PA (US); Aaron Muller, Kutztown, PA (US); Brent Miller, Berwick, PA (US)

(*) Notice: Subject to any disclaimer, the term of this patent is extended or adjusted under 35 U.S.C. 154(b) by 347 days.

(21) Appl. No.: 13/193,797

(22) Filed: Jul. 29, 2011

(65) Prior Publication Data

US 2013/0030716 A1    Jan. 31, 2013

(51) Int. Cl.
  *G01N 31/00* (2006.01)
  *G01N 33/20* (2006.01)
  *G01N 27/416* (2006.01)

(52) U.S. Cl.
  CPC ............ *G01N 33/20* (2013.01); *G01N 27/4163* (2013.01)

(58) Field of Classification Search
  USPC .......................................................... 702/22
  See application file for complete search history.

(56) References Cited

U.S. PATENT DOCUMENTS

| | | | | |
|---|---|---|---|---|
| 4,031,371 A | * | 6/1977 | DeVries | 361/679.4 |
| 5,888,362 A | * | 3/1999 | Fegan, Jr. | 204/400 |
| 6,051,126 A | | 4/2000 | Fegan | 205/790 |
| 6,088,581 A | * | 7/2000 | Bickley et al. | 455/131 |
| 8,339,589 B2 | * | 12/2012 | Jones et al. | 356/71 |
| 2008/0201095 A1 | * | 8/2008 | Yip et al. | 702/85 |
| 2010/0327450 A1 | * | 12/2010 | Uno et al. | 257/762 |

* cited by examiner

*Primary Examiner* — Tung S Lau
*Assistant Examiner* — Xiuquin Sun
(74) *Attorney, Agent, or Firm* — Miller Law Group, PLLC

(57) ABSTRACT

A digital precious metal testing apparatus utilizes a probe that generates a galvanic voltage when an electrical circuit is completed with the object being tested being placed between the probe and the meter test pad formed of a copper pour with a gold coating. A microprocessor signals the percentage of precious metal through an indicator bar of LEDs. A calibration system is provided to enhance the accuracy of the testing apparatus by comparing a test reading from a known test specimen with a corresponding theoretical reading for that specimen. The calibration procedure establishes a recalibration curve from the test reading against which all subsequent readings will be compared to determine the content of precious metal. Calibration of the testing apparatus is initiated with the depression of a calibration switch and is undertaken with each power-up of the meter, with each probe replacement and with any substantial change in environmental conditions.

15 Claims, 8 Drawing Sheets

PRECIOUS METAL TESTING APPARATUS WITH CALIBRATION SYSTEM

BACKGROUND OF THE INVENTION

The present invention relates generally to an apparatus for testing the purity of precious metals, including gold, silver and platinum, and, more particularly, to a recalibration system that improves the operation and accuracy of the testing apparatus.

A precious metal testing apparatus is shown in U.S. Pat. No. 5,888,362, issued to Lloyd V. Fegan, Jr., on Mar. 30, 1999. This testing apparatus provides a portable device that can provide accurate analysis of the quality of the precious metal being tested by utilizing a hand-held probe having an electrode embedded in an electrolyte contained within a reservoir formed in the probe. The testing apparatus generates a galvanic current through the metal being tested from a battery, the strength of the current being proportionate to the quality of the precious metal being tested. In the Fegan patent, a meter circuit measures the extent of galvanic action of dissimilar metals in the presence of an electrolyte, one of the metals being the sample being tested for quality. Thus, the invention is useful for testing the metal content of coins, art objects jewelry, and the like, by reason that the probe can simply be touched against the object being tested to provide a reading representing the quality of the precious metal in the object.

The hand-held probe in the aforementioned precious metal testing apparatus is typically in the form of a pen having a fibrous tip from which a small amount of electrolyte is deposited onto the object being tested. The meter attached to the probe continuously measures the strength of the galvanic current and compares the result with a known point of reference for the type of precious metal being tested, whereby the percentage of precious metal within the object being tested will be know. This measurement process by the meter and pen is completed within a few hundredths of a second, thus providing an efficient manner in which the quality of precious metal can be determined. However, even though the measurement process is fast, the strengths of the galvanic reaction when reacted with gold, silver or platinum are very weak.

Accordingly, slight variations in system parameters are significant enough to reduce the overall accuracy of the meter, and can render the testing apparatus essentially useless. In addition to the electronic and mechanical variations that affect the accuracy of the testing apparatus, variations in operating environment, such as temperature and humidity, also affect the accuracy of the meter. One skilled in the art will recognize that with any galvanic reaction occurring from dissimilar metals and an electrolyte one metal is sacrificed to the other across the electrolyte. As the electrolyte and the sacrificial metal are consumed, the galvanic strength varies. Furthermore, the accuracy of the testing apparatus is impacted negatively over time because the strength of the galvanic reaction decreases with each and every specimen measured. The exhaustion of materials within the pen that are responsible for generating the galvanic strength can be mitigated by replacing an improperly functioning pen probe with a new pen probe. When the pen is replaced, however, the replacement pen will have subtle differences in composition from the pen that has been replaced, which again provides a variation that impacts the accuracy of the testing apparatus.

Calibrating the Fegan precious metal testing apparatus was possible by removing the housing and utilizing a screwdriver or similar instrument to adjust one of the variable resisters in the Fegan circuitry. Testing against a known purity of gold would provide a calibrated reading that would often need further calibration, again requiring the removal of the meter housing and further adjustment of one of the variable resisters. This process was repeated until the Fegan precious metal testing meter was showing the proper results from the known purity sample being tested for the purposes of calibrating the meter. Thus, calibrating the Fegan meter was a complex and time consuming process. Accordingly, accuracy in testing precious metals with the Fegan meter was not consistent as changes in the electrolyte and other environmental factors would deteriorate accurate test results.

A solution for solving the accuracy issues of the aforementioned testing apparatus would be desirable. One possible solution could be a method for recalibrating the testing apparatus to increase accuracy and improve the usable life of the testing apparatus across various manufacturing differences, operating environments, pen replacements, and the number of objects being tested.

SUMMARY OF THE INVENTION

It is an object of this invention to provide a precious meter testing apparatus that overcomes the disadvantages of the known prior art.

It is another object of this invention to provide a precious metal testing apparatus that is digital.

It is a feature of this invention that the precious metal testing apparatus includes a meter box having a test pad and a detachable pen probe having a fiber tip coupled with an electrolyte to complete an electrical circuit with an object containing precious metal placed in contact between the fiber tip and the test pad.

It is an advantage of this invention that the pen probe incorporates a galvanic reaction apparatus that generates a galvanic voltage in direct proportion to the percentage of precious metal content within an object being tested.

It is another feature of this invention that the test pad id formed of a copper pour with a coating of gold over the top surface thereof.

It is another advantage of this invention that the test pad establishes a baseline galvanic reaction by touching the fiber tip of the probe directly on the test pad.

It is still another advantage of this invention that the test pad stabilizes the galvanic reaction within the pen probe by eliminating noise and galvanic peaking.

It is yet another advantage of this invention that the gold coating on the copper test pad limits the corrosion of the copper test pad due to the working environment by isolating the test pad from the electrolyte within the fiber tip of the probe.

It is yet another feature of this invention that the meter box incorporates a microprocessor and electronic circuitry interconnecting the microprocessor with digital indicators of various functions of the testing apparatus.

It is still another object of this invention to provide a calibration system for the testing apparatus that is easily operated and effective in use to establish a high confidence in the accuracy of the test readings on objects that contain precious metal.

It is a feature of this invention that the calibration system includes a calibration switch to selectively initiate the calibration procedure.

It is another feature of this invention that the calibration procedure starts with the testing of a known quality test specimen to generate a test reading that is compared to a theoretical reading stored in a look-up table in the microprocessor.

It is still another feature of this invention that the calibration procedure generates a recalibration curve for different percentages of precious metal content from an algorithm corresponding to the theoretical readings in the look-up tables to which all subsequent test readings are compared.

It is yet another advantage of this invention that the accuracy of the testing apparatus is improved by a recalibration of the testing operation.

It is yet another feature of this invention that the calibration procedure is conducted each time the testing apparatus is powered up.

It is a further advantage of this invention that the recalibration curve against which all subsequent test measurements are compared is generated from a single test reading of a known quality test specimen.

It is still a further advantage of this invention that the calibration of the test readings provides correction of differences from manufacturing tolerances, variations in operating environment, and differences in galvanic reaction's metals and electrolyte, and also the longevity of the pen probe usage.

It is a further feature of this invention that a degradation of the pen probe can be detected by the differential between the test reading of the known quality test specimen and the corresponding theoretical reading.

It is yet a further advantage of this invention that the microprocessor can signal for the replacement of the pen probe if the differential between the test reading of the known quality test specimen and the corresponding theoretical reading is greater than a predetermined percentage.

It is still another advantage of this invention that the exhaustion of materials in the pen probe responsible for the generation of the galvanic voltage can be mitigated by replacing the pen probe with a new pen probe, which would require calibration due to manufacturing tolerances within the pen probes can affect accuracy of the testing apparatus.

It is yet another object of this invention to provide a testing apparatus for determining the content of precious metal within an object being tested, that is durable in construction, inexpensive of manufacture, carefree of maintenance, facile in assemblage, and simple and effective in use.

It is a further object of this invention to provide a calibration system for a precious metal testing apparatus that is simple and effective in use and operation to increase the accuracy of the testing apparatus.

These and other objects, features and advantages are accomplished according to the instant invention by providing a digital precious metal testing apparatus, which utilizes a probe that generates a galvanic voltage when an electrical circuit is completed with the object being tested between the probe and the meter test pad formed of a copper pour with a gold coating. A microprocessor signals the percentage of precious metal through an indicator bar of light-emitting diodes. A calibration system is provided to enhance the accuracy of the testing apparatus by comparing a test reading from a known test specimen with a corresponding theoretical reading for that specimen. The calibration procedure establishes a recalibration curve from the test reading against which all subsequent readings will be compared to determine the content of precious metal. Calibration of the testing apparatus is initiated with the depression of a calibration switch and is undertaken with each power-up of the meter, with each probe replacement and with any substantial change in environmental conditions.

BRIEF DESCRIPTION OF THE DRAWINGS

The advantages of this invention will be apparent upon consideration of the following detailed disclosure of the invention, especially when taken in conjunction with the accompanying drawings wherein.

DETAILED DESCRIPTION OF THE PREFERRED EMBODIMENT

Figure 1:
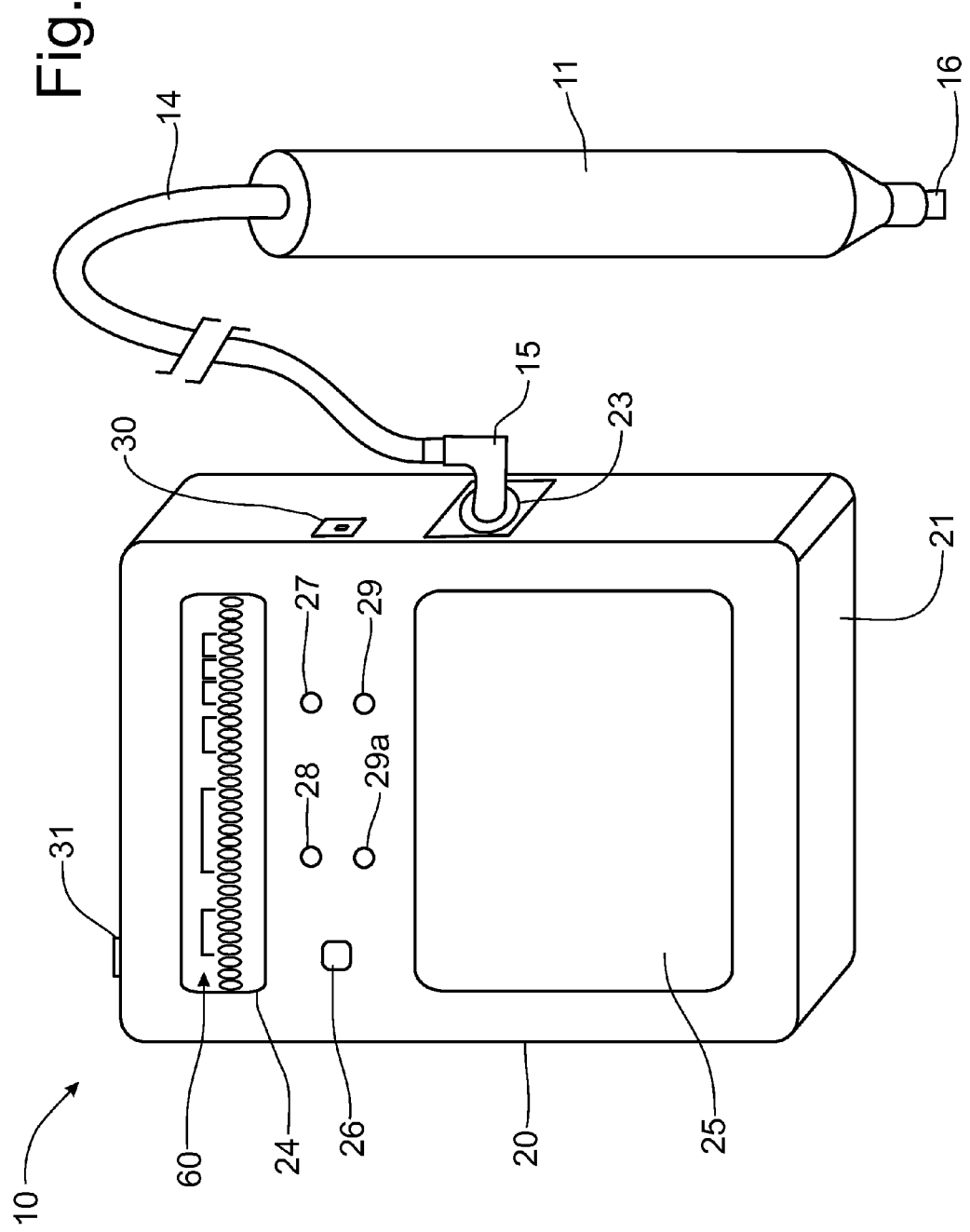
FIG. 1 is a schematic diagram of a testing apparatus incorporating the principles of the instant invention and including a pen probe electrically coupled to a meter to measure the galvanic current generated by the testing apparatus and provide an output indicating the purity of the precious metal being tested.
Figure 2:
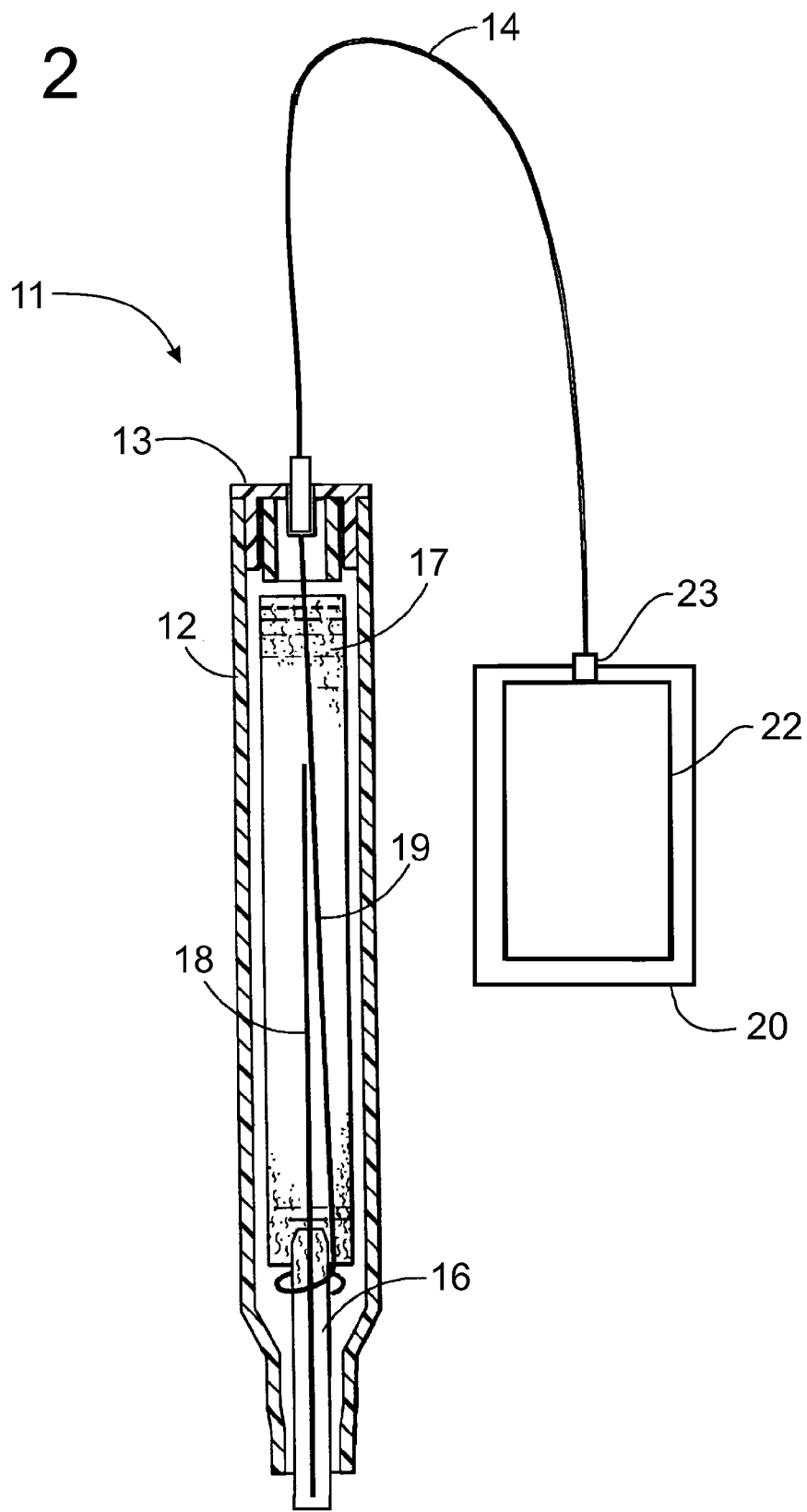
FIG. 2 is a vertical cross-sectional view of a pen probe forming a part of the testing apparatus incorporating the principles of the instant invention.
Figure 3:
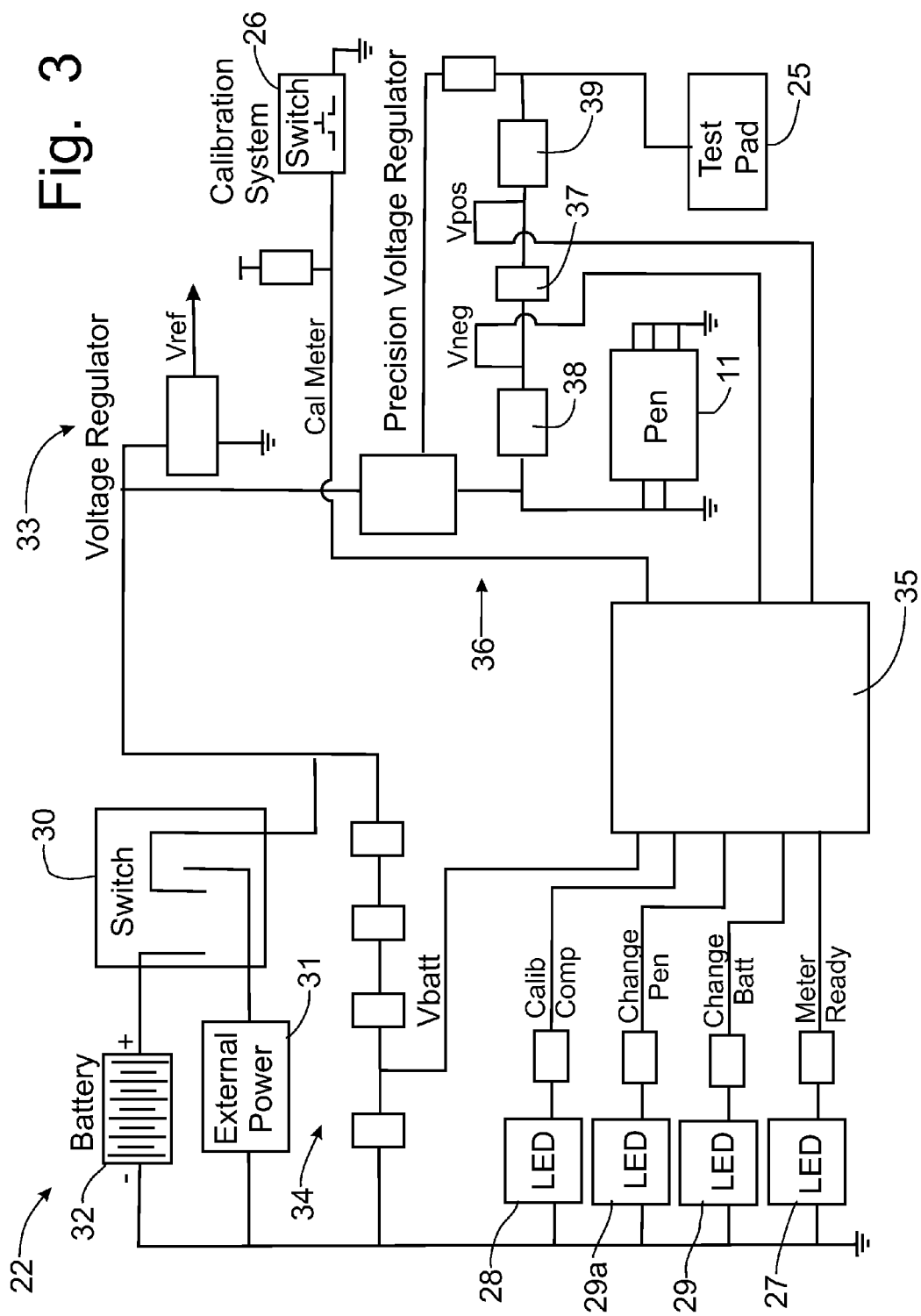
FIG. 3 is a schematic view of the electronic circuit forming the apparatus measuring the galvanic current generated through the testing procedure.

Referring now to FIGS. 1-3, a testing apparatus for analyzing the quality of the precious metal within an object being tested can best be seen. This testing apparatus 10 incorporates the principles of the instant invention by utilizing a recalibration system to enhance the accuracy of the continued use of the testing apparatus 10. The principle for the testing apparatus 10 is described in greater detail in the aforementioned U.S. Pat. No. 5,888,362, the content of which is incorporated herein by reference.

In general, the testing apparatus 10 is used to analyze the content or gold or other precious metal and is based on developing and measuring an electromotive force (EMF) due to electrical conduction between two dissimilar metals or metal alloys, namely an electrode and the object to be analyzed. The galvanic voltage results from the difference in availability of electrons in the different metals or alloys, and provides a net current when the metals or alloys are coupled through an electrolyte. The galvanic voltage generated by the dissimilar metals or metal alloys is generated using the touch probe 11 of the invention, and is measured by subtracting the galvanic EMF from that of a battery or similar reference voltage level at a constant reverse polarity voltage. The galvanic voltage generated is directly related to the proportion of the gold or other precious metal content of the object being tested and, thus, provides a means by which the purity of the sample can be determined.

An exemplary embodiment of the pen probe 11 forming part of the testing apparatus 10 is shown in FIG. 2, which is a cross-sectional view of the exemplary hand-held pen probe 11. The pen probe 11 is preferably formed with a generally cylindrical body 12, which can be made of plastic or other substantially electrically non-conductive material. A top cap 13 is coupled to an electrical wire 14 fitted with a jack 15 to facilitate a detachable electrical connection of the pen probe 11 to the circuitry 22 within the meter 20. The end of pen probe 11, which is placed into contact with the object to be tested, is formed as a fiber tip 16 that is in communication with a reservoir 17 containing a supply of electrolyte, such as a saturated solution of ammonium chloride, or other solutions as is known for conventional galvanic testing techniques. The fiber tip 16 is provided with a thin platinum wire 18, which is preferably embedded into the fiber tip 16 and extends into the reservoir 17. A second thin platinum connecting wire 19 couples the platinum wire 18 to the wire 14 at the top cap 13 of the pen probe 11.

The testing apparatus 10 further includes a meter 20 including a housing 21 in which is mounted a printed circuit board 22 including a port 23 to which the jack 15 can be detachably connected. Also electrically connected to the circuitry 22 is a test pad 25 that is preferably formed as a copper pour having a surface coating of gold. This configuration of the test pad 25 allows the testing apparatus 10 to set-up a baseline galvanic reaction for the zero point of the testing apparatus 10, which can be accomplished by the operator touching the fiber tip 16 of the pen 11 directly to the test pad 25. The test pad configuration also stabilizes the galvanic reaction during the calibration procedure and during test measurements by eliminating noise and galvanic peaking. The gold coating also limits the corrosion of the copper due to the working environment and by isolating the copper from the electrolyte solution within the fiber tip 16.

The meter 20 is also constructed with a light-emitting diode (LED) indicator bar 24 that reflects the results of the measurement of the galvanic current, as will be discussed in greater detail below. In addition, the housing 21 supports a calibration switch 26 that is operable to initiate the calibration procedure, as will be described in greater detail below. The housing 21 also supports four LEDs that reflect the status of the operation of the testing apparatus 10, including a first LED 27 to indicate the power is turned on and the testing apparatus 10 is ready, a second LED 28 to indicate that the calibration procedure is finished, a third LED 29 to indicate that the battery is low on power and needs to be replaced, and a fourth LED 29*a* to indicate that the pen probe 11 needs to be replaced. The meter 20 has a three position on/off switch 30 that is movable to an off position, an external power position, and a battery power position. The housing 21 also supports a port 31 for connection to a source of external power, such as 110 VAC electrical current through the use of an adapter (not shown).

The circuitry 22 is reflected in the schematic diagram of FIG. 3. Either a battery 32 or a source of external electrical power connected through the port 31 provides an electrical current into the circuitry 22 that is regulated to a base reference voltage (Vref) by the voltage regulator 33. The microprocessor 35 monitors the voltage divider circuit 34 to ensure sufficient operational voltage (Vbatt) to run the testing apparatus 10. When operational voltage drops below a minimum requirement, the microprocessor 35 illuminates the third LED 29 to indicate a battery change is needed. Once the microprocessor 35 confirms that sufficient operational voltage is available and that the voltage (Vref) is properly regulated, the first LED 27 is illuminated to indicate that the testing apparatus 10 is ready to start operation.

Once calibrated, as will be described in greater detail below, the testing apparatus 10 is able to determine the quality (i.e. precious metal content) of an object. The object to be tested is placed onto the test pad 25 and the pen probe 11 is moved into engagement with the object by touching the exposed fiber tip 16 on the object, completing the electrical circuit within the meter 20. A galvanic reaction then occurs within the pen probe 11, creating a weak voltage within a range of approximately 60 millivolts, which is detected by the microprocessor 35 monitoring the voltage (Vneg and Vpos) in the metering circuit 36 on opposite sides of the resister 37. The galvanic voltage generated in the pen probe 11 by completing the electrical circuit in the meter 20 through the object being tested is directly proportional to the precious metal content within the object and opposes the forward biased diodes 38, 39 in the metering circuit 36. The opposition to this forward bias decreases the voltage across the resister 37. Thus the galvanic voltage (Vdiff) is the difference between the voltage (Vneg and Vpos) on opposite sides of the resister 37.

The microprocessor determines this galvanic voltage (Vdiff) and compares the galvanic voltage with known galvanic responses stored in a look-up table within the microprocessor 35, Since the galvanic reaction (Vdiff) is directly proportionate to the percentage of precious metal within the object being tested, the microprocessor can determine the percentage from the values on the look-up table and illuminate the LEDs in the indicator bar corresponding to the percentage of precious metal detected in the measurement. Thus, the indicator bar will provide an indication of the Karat weight of the gold in the object, but can also determine the percentage of silver and platinum within the object if the object is not made of gold.

The microprocessor 35 incorporates a system for automatically calibrating the subtle differences in the testing apparatus 10, including manufacturing irregularities within the pen probe 11 that normally occur, as well as differences relating to the operating environment, such as changes in the temperature and humidity, and the longevity of use of the pen probe 11. The calibration system has two primary components, look-up tables stored within the electronic microprocessor 35 and a recalibration procedure operated by the electronic microprocessor 35. The look-up tables store the galvanic strengths of gold, silver and platinum that have been normalized for a new pen probe 11 having a full sacrificial metal wire 18 and a full reservoir 17 of electrolyte, under the operating environmental conditions of a temperature at 25° C. and 40% humidity. The calibration procedure realigns the testing apparatus 10 to known operating parameters based upon a current measurement of a known parameter.

Figure 10:
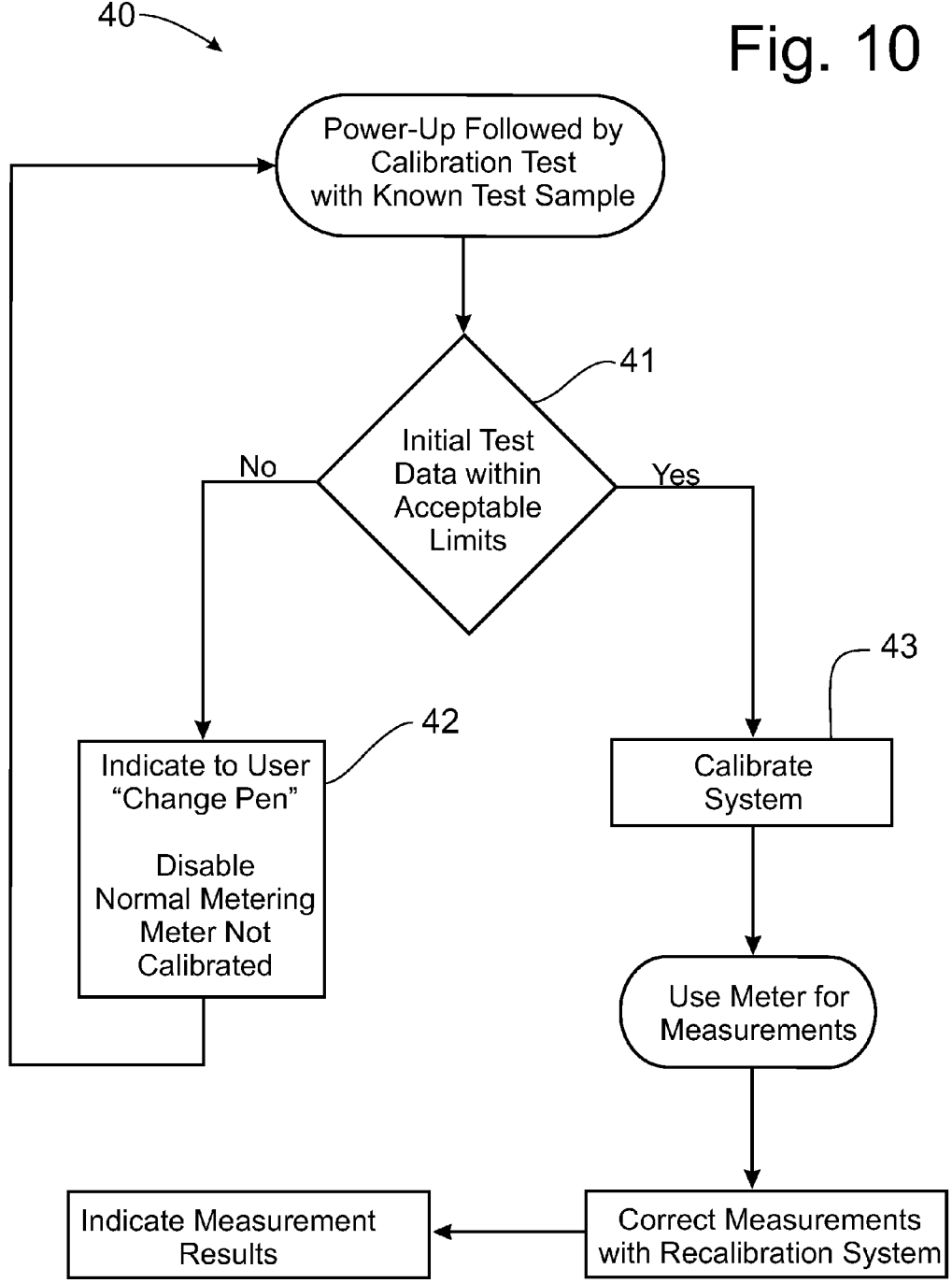
FIG. 10 is a logic flow diagram of the initial start-up sequence for the meter.

As is reflected in FIG. 10, the testing apparatus 10 must be calibrated at initial power-up to establish the base operating reference point for the recalibration system 40. The calibration system 40 starts with the placement of a known test specimen (not shown), having a known specific percentage of precious metal, on the test pad 25 and touches the test specimen with the pen probe 11. The first test is at step 41 to determine if the initial reading of the galvanic reaction corresponding to the known specimen is within normal acceptable limits. If not, the microprocessor illuminates the fourth LED 29*a* at step 42 to provide an indication that the pen probe 11 needs to be replaced. Assuming that the initial reading is acceptable, the operator then activates the calibration system 40 at step 43 by depressing the momentary switch 26 to initiate the calibration procedure.

Figure 6:
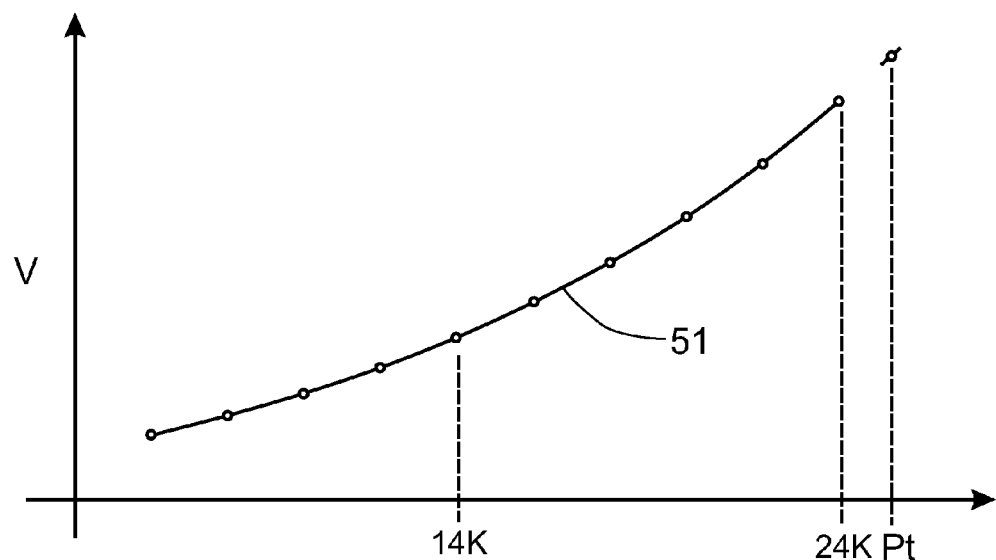
FIGS. 6-9 are graphic representations of the calibration procedure.
Figure 7:
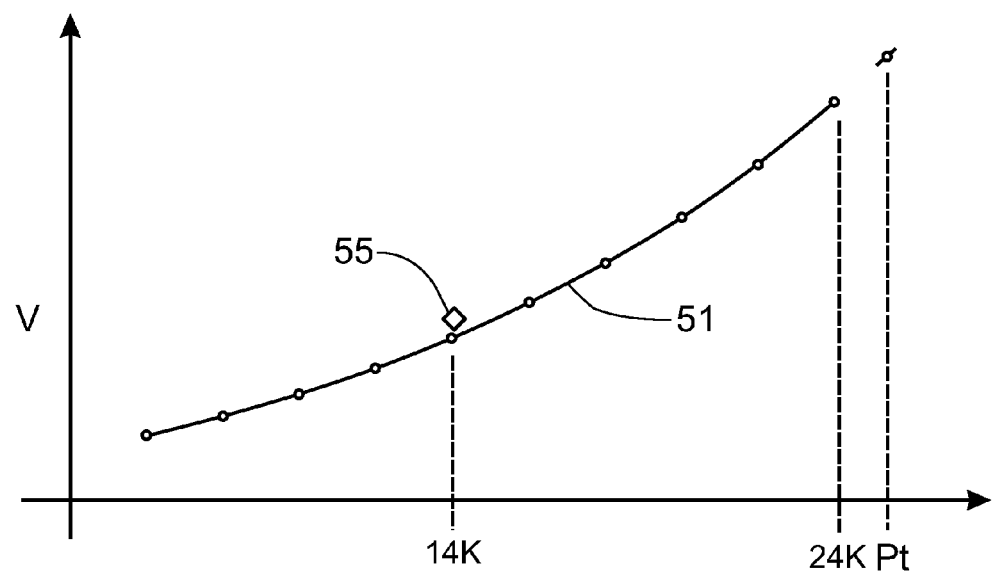
Figure 8:
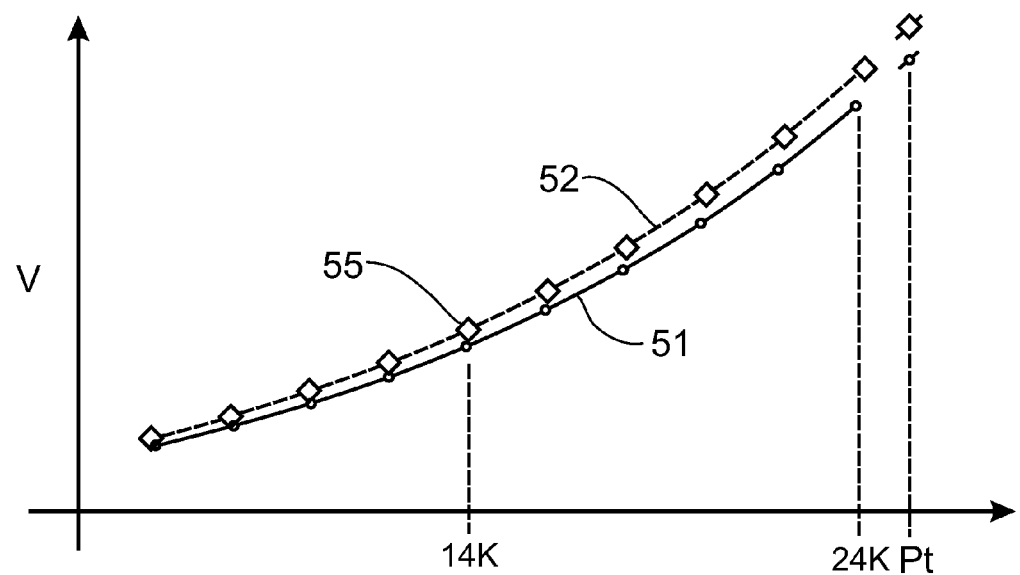
Figure 9:
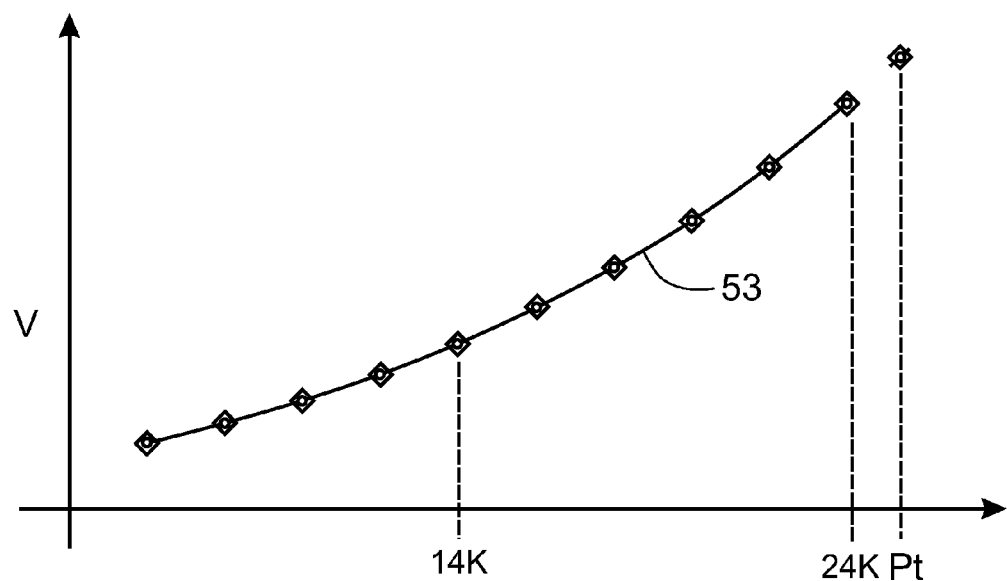
Figure 11:
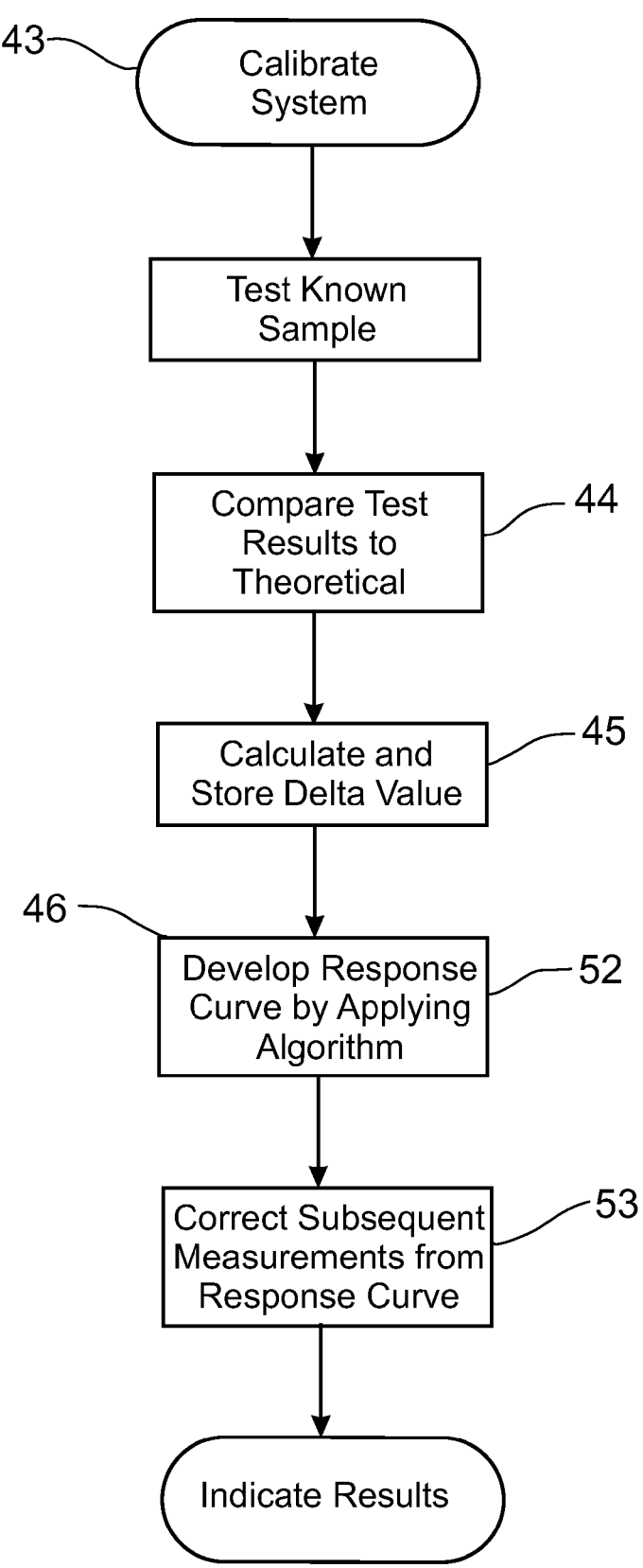
FIG. 11 is a logic flow diagram for the recalibration procedure.

As depicted in FIG. 11, the microprocessor 35 compares at step 44 the initial reading of the galvanic reaction of the known specimen to the theoretical value shown for the known test specimen within the look-up table within the microprocessor 35. Assuming that there is a difference between the initial reading and the corresponding theoretical value from the look-up table, the delta value is calculated and stored in the microprocessor 35 at step 45, as shown in FIG. 7 as data point 55. The microprocessor 35 then develops at step 46 a response curve 52 using the algorithm corresponding to the curve 51 of the theoretical values from the look-up table, as is represented in FIGS. 6 and 8. This response curve 52 is then recalibrated, as is represented in FIG. 9, by the differential between the theoretical value curve 51 and the response curve 52 to develop a recalibration curve 53 that is used to correct all subsequent readings of objects being tested, until the next calibration procedure is undertaken.

Figure 4:
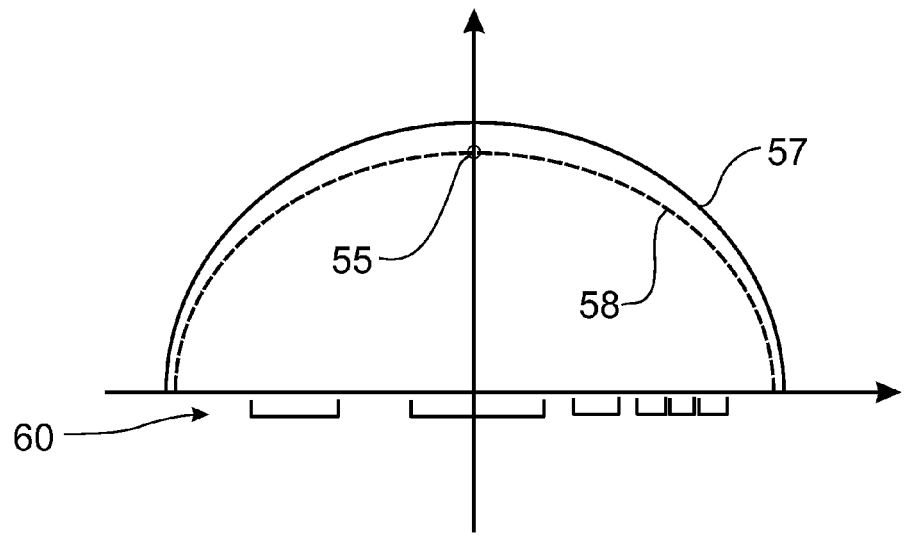
FIG. 4 is a graphic representation of the calibration process incorporating the principles of the instant invention.
Figure 5:
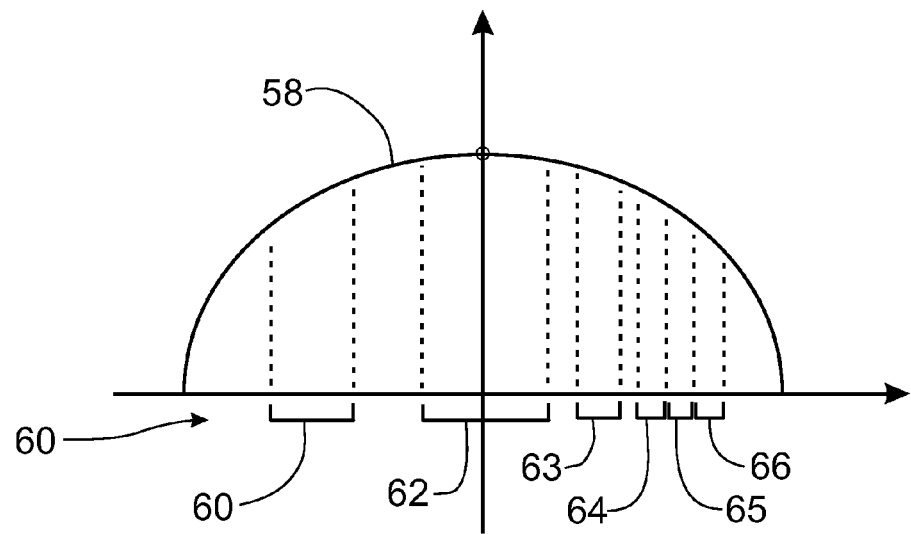
FIG. 5 is a graphic representation of the corrected curve following the calibration procedure.

The end result of the recalibration procedure is depicted in FIGS. 4 and 5. The theoretical galvanic voltages within the look-up tables can be plotted on a graph somewhat as a parabolic curve 57. The initial reading 55 can be above or below the corresponding theoretical reading along the Y-axis. When plotted, the response curve 52 results in a calibrated parabolic curve 58 which is then used to signify the Karat weight of the object being subsequently tested by reference to Karat bands 60 with 10K gold falling within the band 61, 14K gold falling into band 62, 18K gold falling in band 63, 22 K gold falling into band 64, 24K gold falling into band 6556, and platinum falling into band 66. The Karat bands 60 correspond to the LED brackets depicted on the indicator bar 24 on the meter 20.

Because of the changes in the variables involved in the testing of precious metal with the testing apparatus 10, the calibration procedure should be run each time the meter 20 is powered up. Furthermore, the ion exchange in the electrolyte can deteriorate the sensitivity of the testing apparatus 10; therefore, the calibration procedure should also be run after a significant number of objects have been tested even if the meter has not been powered down. Likewise, moving the meter 20 from one environmental situation into a significantly different environmental situation would preferably incur an invoking of the calibration procedure. The calibration of the meter 20 only takes a few seconds and should not be an impediment to implement when accuracy is important to the operator. This process of measuring the precious metal content of an object is completed, start to finish, in just a few hundredths of a second. Thus, an extremely efficient method is provided to characterize samples containing precious metals.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiment of the invention; however, concepts, as based upon the description, may be employed in other embodiments without departing from the scope of the invention.

Having thus described the invention, what is claimed is:

1. A testing apparatus for determining the content of precious metal within an object being tested, comprising:
   a meter including:
     a microprocessor having look-up tables stored therein;
     an indicator bar operably coupled to said microprocessor;
     a source of electrical power connected to said microprocessor;
     a test pad formed as a copper pour with a gold coating thereon; and
     an electronic circuit interconnecting said microprocessor, said indicator bar, said source of electrical power and said test pad;
   a probe connected to said meter and including:
     a casing;
     a reservoir mounted within said casing and containing a supply of electrolyte;
     a fiber tip supported in said casing and having a first end coupled to said reservoir to receive electrolyte therefrom and a second end exposed from said casing;
     an electrical connector interconnecting said pen probe and said metering device; and
     a galvanic reaction apparatus mounted within said reservoir and having a first member connected to said fiber tip and a second member connected to said electrical connector, said galvanic reaction apparatus generating a galvanic voltage when said fiber tip completes an electrical circuit with said test pad; and
   a calibration system operably associated with said microprocessor to operate a calibration procedure that utilizes a calibration test reading from an application of said fiber tip of said probe to a known test specimen and compares said calibration test reading with a theoretical test reading stored in said look-up tables where said theoretical test reading corresponds to said known test specimen, said calibration procedure developing a calibrated response curve by applying an algorithm corresponding to the theoretical test reading in comparison to said calibration test reading so that all subsequent test readings will be adjusted to said calibrated response curve, said calibrated response curve comprising a response curve for said known test specimen from the look-up tables adjusted by the difference between said calibration test reading and said theoretical test reading, said calibrated response curve being used for all subsequent test readings for said probe until said calibration system is subsequently operated to create a new calibrated response curve.

2. The testing apparatus of claim 1 wherein said calibration system includes a switch mounted on said meter to initiate said calibration procedure.

3. The testing apparatus of claim 1 wherein said electronic circuit includes a metering circuit that identifies a voltage difference on opposite sides of a resister between two forwardly biased diodes due to the galvanic voltage generated in the probe during test operations.

4. The testing apparatus of claim 3 wherein said known test sample is 14K gold.

5. The testing apparatus of claim 4 wherein said source of electrical power is one of a battery and an external source of electrical power coupled to said electronic circuit by an external port.

6. The testing apparatus of claim 5 wherein said indicator bar comprises an array of light-emitting diodes that said microprocessor illuminates in response to the test reading from an object interconnecting said test pad and said fiber tip of said probe.

7. A calibration system for a precious metal testing apparatus having an electronic circuit interconnecting a microprocessor, a test pad, an external probe, and a source of electrical power for testing the precious metal content of an object, said calibration system comprising:
   a calibration switch mounted on said testing apparatus to initiate a calibration procedure;
   a metering circuit interconnecting said test pad and said probe to detect a galvanic voltage generation within said test probe when a known quality test specimen is electrically coupled between said test pad and said probe to generate an initial reading indicative of said galvanic voltage;
   said microprocessor comparing said initial reading with a theoretical reading corresponding to said test specimen stored within look-up tables in said microprocessor, said initial reading being used to determine normalization of said probe which is attained when said microprocessor confirms that said initial reading is within predefined acceptable limits from said theoretical reading; and
   said microprocessor operating said calibration procedure after said probe has been normalized by calculating the difference between the initial reading and the theoretical reading and applying an algorithm corresponding to said theoretical reading from said look-up tables to said initial reading to generate a recalibrated response curve for different percentages of precious metal, said recalibrated response curve comprising a response curve using said probe having current operational parameters for said known test specimen from the look-up tables adjusted by the difference between said initial reading and said theoretical reading, all subsequent test readings of objects being tested being compared to said recalibrated response curve to determine the precious metal content of each subsequently tested object, said recalibrated response curve being used for all subsequent test readings until said calibration system is subsequently operated to create a new recalibrated response curve corresponding to a new said probe or changes in said operational parameters.

8. The calibration system of claim 7 wherein said precious metal testing apparatus has an on/off switch, said calibration procedure being required each time said on/off switch is moved from an off position to an on position to power-up the precious metal testing apparatus.

9. The calibration system of claim 7 wherein said calibration procedure can be initiated anytime the precious metal testing apparatus is powered by electrically coupling the known test specimen between the test pad and the probe and depressing the calibration switch.

10. The calibration system of claim 7 wherein the microprocessor rejects the test reading and provides an indication that the probe should be replaced if the test reading deviates from the corresponding theoretical reading in the look-up tables by a predetermined percentage.

11. The calibration system of claim 7 wherein the known quality test specimen is a 14K gold specimen.

12. A calibration method of calibrating a precious metal testing apparatus having an electronic circuit interconnecting a microprocessor, a test pad, an external probe, and a source of electrical power for testing the precious metal content of an object, comprising the steps of:
electrically coupling a known quality test specimen between the test pad and the probe to generate a galvanic voltage within said probe;
detecting the galvanic voltage by a metering circuit within said electronic circuit and generating an initial test reading received by the microprocessor;
comparing the initial test reading to a theoretical reading for the known quality test specimen stored in look-up tables within said microprocessor to determine normalization of said probe when said initial test reading is within a predetermined acceptable limit from said theoretical reading;
after normalization of said probe, calculating a delta differential between the initial test reading and the corresponding theoretical reading;
storing the delta differential in the microprocessor; and
utilizing the delta differential to recalibrate any subsequent readings taken of objects to be tested for precious metal content by applying an algorithm corresponding to a graphical plotting of different percentages of precious metal content corresponding to the theoretical reading stored in said look-up tables to generate a recalibrated response curve for use during subsequent operations of said precious metal testing apparatus to compare all said subsequent readings taken of objects to be tested for precious metal content until said calibration method is subsequently operated, said recalibrated response curve comprising a response curve for said known test specimen from the look-up tables adjusted by the delta differential between said initial reading and said theoretical reading, changes in said probe including changes in operational parameters for said probe requiring the creation of a new recalibrated response curve.

13. The method of claim 12 wherein said calibration method is undertaken each time the precious metal testing apparatus is powered-up.

14. The method of claim 12 further comprising the step of:
after said calculating step, rejecting said test reading if said delta differential is greater than a predetermined amount; and
signaling from the microprocessor that the probe needs to be replaced before the calibration method can be continued.

15. The method of claim 12 wherein said known quality test specimen is formed from 14K gold.

* * * * *